Oct. 25, 1938. M. H. HORVATH Plant Pat. 296
ROSE
Filed Sept. 1, 1937
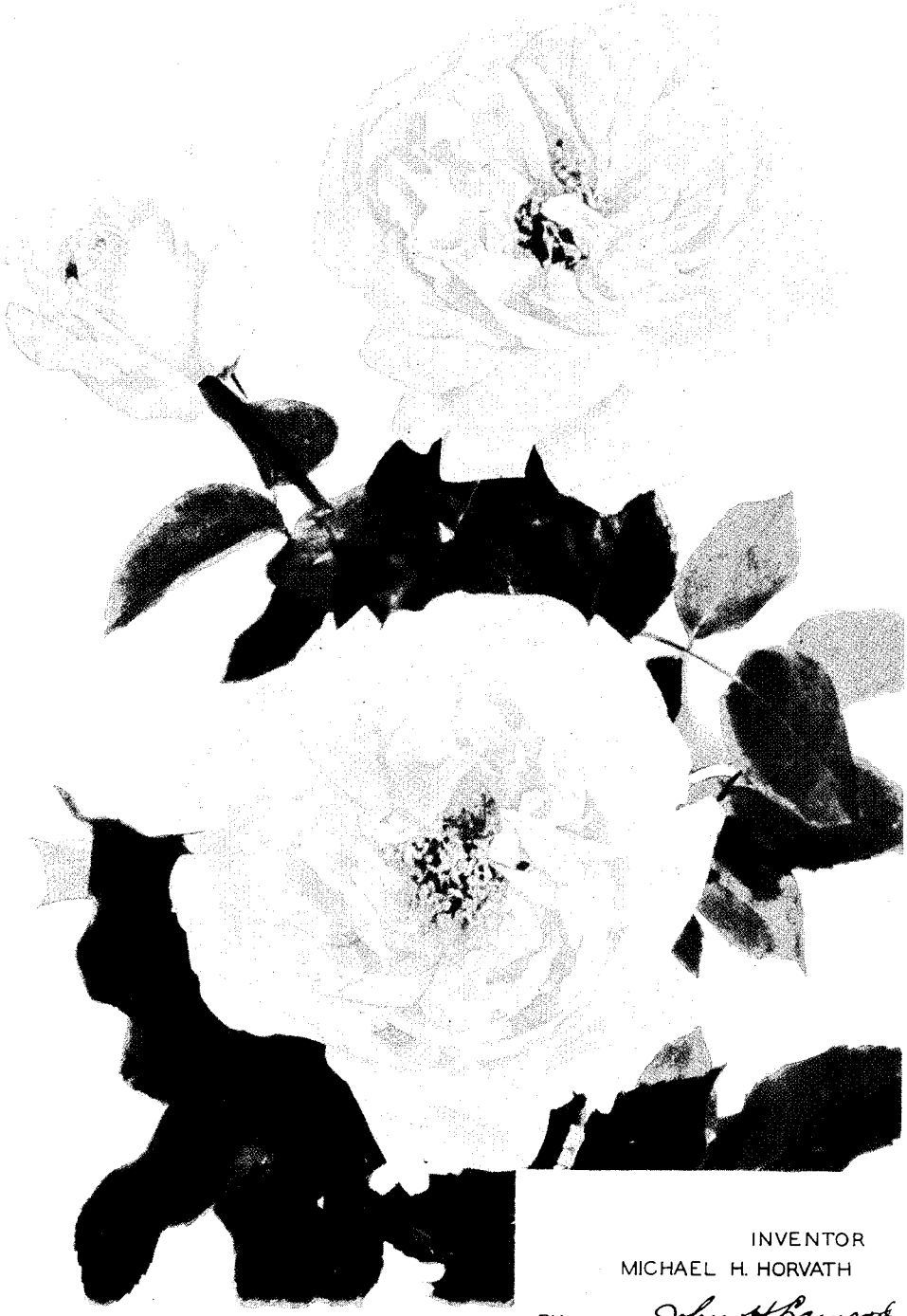
INVENTOR
MICHAEL H. HORVATH
BY John H. Bennett,
HIS ATTORNEY Patented Oct. 25, 1938

Plant Pat. 296

UNITED STATES PATENT OFFICE

296

ROSE

Michael H. Horvath, Mentor, Ohio

Application September 1, 1937, Serial No. 162,063

1 Claim. (Cl. 47—61)

This invention relates to a new variety of rose, a "Rosa Setigera Hybrid," produced by crossing a rose variety, "Dubloons," as the female parent, with a rose variety, "Chas. P. Kilham," as the male parent. The new variety has been successfully asexually reproduced in quantities.

The new climbing rose is distinctly a hardy variety. It grows without protection in the temperate region, and it can be successfully grown with protection in the colder regions where the growing of roses has been impossible or exceedingly difficult.

An appearance of noble ruggedness is produced by the shrub of the climbing plant and it grows to a height of fourteen feet or more. The rich shining bronzy green colored leaflets, comparable to Maerz & Paul Plate No. 24 C–9, are larger than those of the Mahonia and of the Orange Grape, but they possess unique ornamental qualities and add materially to the attractiveness of the plant.

The flowers of this variety are actually large in comparison with flowers of known rose varieties, being five to six inches across when fully open and containing some fifty to fifty-five petals. Spur branches of from one to two feet long, growing from the main stock and from laterals, support the abundance of flowers produced by the plant. These branches are relatively stiff and sufficiently strong to keep the flowers from drooping.

The buds are slow in opening, but upon opening to full bloom, the flowers have a characteristically long life and, though large, the flowers are refined and equal to the finest hybrid tea rose known. The flowers are of a clear deep rose pink color, comparable to "Wild Rose" of Maerz & Paul Plate No. 3 I–7, of the same shade as the "Dame Edith Helen" variety, and they are carried by stems which are heavily thorned.

The drawing further illustrates many of the characteristics which are not found in the parent stock or known rose varieties, but which add to the value of the plant as a shrub and increase its beauty, such as, the semi-globular shape of bud, the very firm and heavy texture of petals, the oval shape of foliage having deeply marked ribs and veins and the glabrous character of the stems supporting the flowers.

Having now fully shown and described my new rose, and the mode of its production, what I claim and desire to secure by Letters Patent of the United States, is:

A climbing rose as herein shown and described and distinguished by the hardy character and rugged appearance of the shrub, rich, shining, bronzy green leaflets possessing unique ornamental qualities and larger in size than the Mahonia and the Orange Grape, flower growth, and large clear deep rose pink flowers of a refined and enduring quality abundantly produced and well supported on relatively stiff spur branches.

MICHAEL H. HORVATH.